United States Patent [19]
Chapman

[11] 4,182,924
[45] Jan. 8, 1980

[54] HF ALKYLATION PROCESS UTILIZING FRACTIONATION ZONES AT DIFFERENT PRESSURES AND INCLUDING INDIRECT HEAT EXCHANGE

[75] Inventor: Charles C. Chapman, Bartlesville, Okla.

[73] Assignee: Phillips Petroleum Company, Bartlesville, Okla.

[21] Appl. No.: 914,823

[22] Filed: Jun. 12, 1978

[51] Int. Cl.² .............................................. C07C 3/54
[52] U.S. Cl. .................................. 585/712; 585/719; 585/723
[58] Field of Search ................... 260/683.48, 683.42, 260/683.43

[56] References Cited
U.S. PATENT DOCUMENTS

| | | | |
|---|---|---|---|
| 3,204,010 | 8/1965 | Van Pool | 260/683.42 |
| 3,204,011 | 8/1965 | Hettick et al. | 260/683.42 |
| 3,763,022 | 10/1973 | Chapman | 260/683.48 |
| 3,857,904 | 12/1974 | Chapman | 260/683.48 |
| 3,925,501 | 12/1975 | Putney et al. | 260/683.48 |
| 3,957,901 | 5/1976 | Chapman | 260/683.43 |

Primary Examiner—George Crasanakis

[57] ABSTRACT

An HF alkylation-fractionation system for the separation of the hydrocarbon phase separated from the HF alkylation effluent by passing the hydrocarbon phase first to a prefractionation zone operated at low pressure, followed by fractionation of both overhead and bottoms from the prefractionation zone at higher pressures and temperatures, and utilization of the high temperature streams obtained from the higher pressure fractionations as sources of heat for indirect heat exchange of the prefractionation zone and feed to at least one of the subsequent fractionations.

5 Claims, 1 Drawing Figure

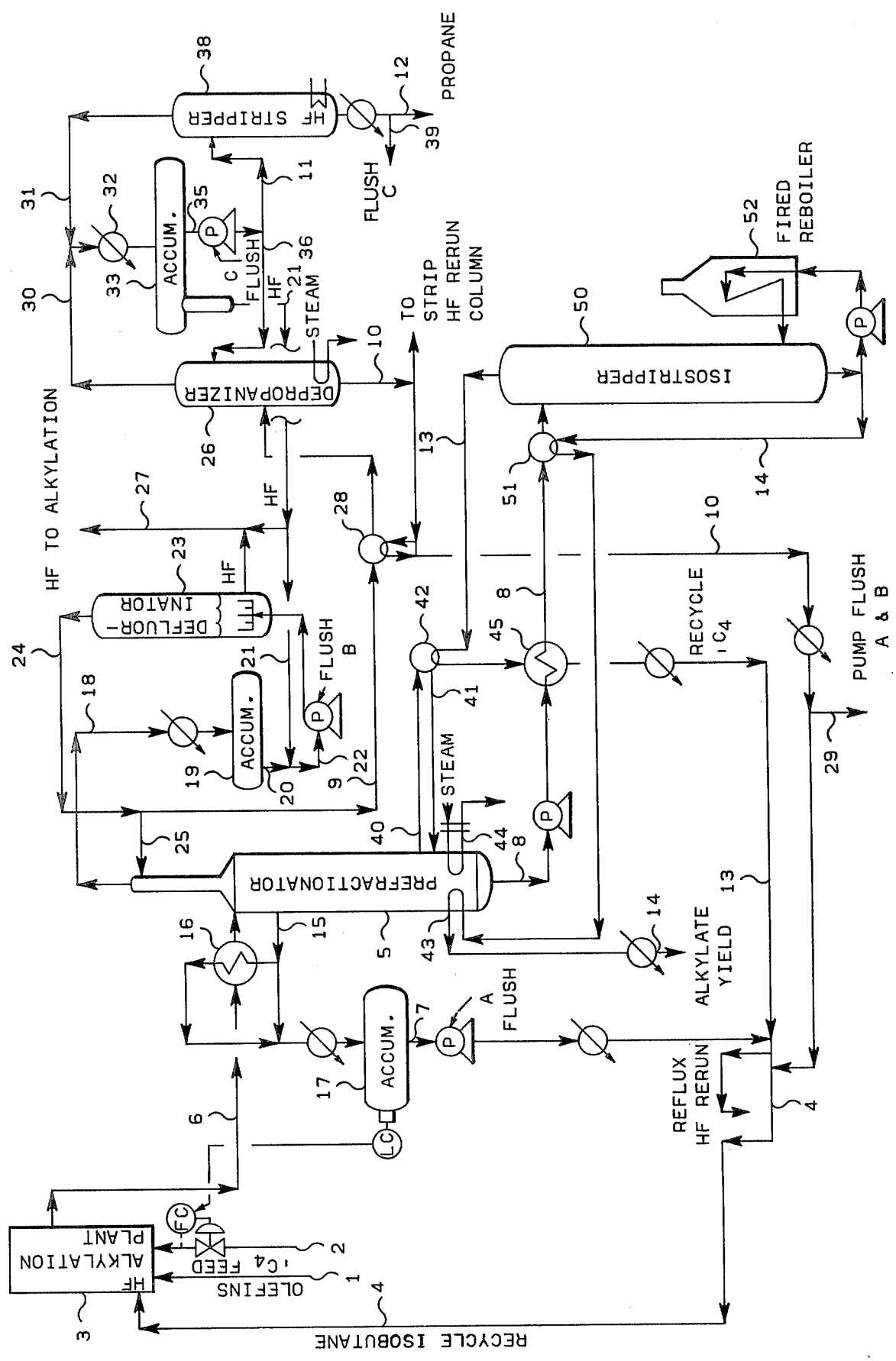

HF ALKYLATION PROCESS UTILIZING FRACTIONATION ZONES AT DIFFERENT PRESSURES AND INCLUDING INDIRECT HEAT EXCHANGE

This invention relates to an HF alkylation process and the recovery of the produced hydrocarbon phase in a more efficient manner. In accordance with another aspect, this invention relates to a fractionation system employing low pressures in an initial fractionation, followed by high pressures in subsequent fractionations for the separation of individual streams from the hydrocarbon phase obtained from an HF alkylation process. In accordance with another aspect, streams separated from the high pressure fractionation zones are used as sources of indirect heat exchange fluid for the low pressure fractionation and indirect heat exchange for feed to at least one of the high pressure fractionation zones. In accordance with a further aspect, the hydrocarbon phase separated from an alkylation effluent is subjected to prefractionation at fractionation conditions of temperature and pressure lower than conventionally employed so as to recover a bottoms stream comprising isoparaffin and alkylate substantially free of HF so that the bottoms stream can be subjected to high temperature and pressure in a subsequent fractionation without corrosion problems and at the same time taking advantage of heat conservation by utilizing the high temperature streams as sources of indirect heat exchange for other units in the system.

As is well known, hydrocarbon products can be produced by alkylation reactions involving the combination of condensation of two dissimilar hydrocarbon reactants in the presence of suitable catalytic agents. Although various types of alkylate products can be obtained by employing various types of reactants, the alkylation of low boiling isoparaffins such as isobutane and isopentane with low boiling olefins such as ethylene, propylene, butene, pentene, and the like for the production of various fuels has become of particular importance. Liquid hydrogen fluoride (hydrofluoric acid) has found favor as a catalyst in this type of reaction.

The alkylation of isobutane with olefins is representative of this type of reaction and has been commonly carried out by feeding isobutane and olefin feedstocks in the liquid state along with hydrofluoric acid to an alkylation reactor such as a riser-reactor. The reaction product stream is then passed to various separation zones such as an HF stripper, an isostripper, and a depropanizer in order to recover the various components of the hydrocarbon phase separated from the alkylation effluent. The energy requirements for heating the various separation zones and streams are great, and it would be desirable due to the high cost of energy to use an energy-conserving alkylation process. The present invention is directed to such an energy-conserving process.

Accordingly, an object of this invention is to provide an improved alkylation process.

Another object of this invention is to utilize available heat in an HF alkylation plant in a more efficient manner.

A further object of this invention is to reduce the energy costs in an HF alkylation-fractionation system.

A further object of this invention is to provide an HF alkylation-fractionation system having minimum corrosion problems.

Other aspects, objects, and the several advantages of this invention will become apparent to those skilled in the art upon a study of the specification, the drawing, and the appended claims to the invention.

In accordance with the invention, an HF alkylation-fractionation system is provided for the separation of the hydrocarbon liquid phase separated from the alkylation effluent comprising a prefractionation zone operated at lower pressures than other units in the separation system, followed by an isostripper zone and a depropanizing zone, both operated at higher pressures than the prefractionation zone.

In accordance with one embodiment of the invention, the overhead and bottoms streams obtained from the isostripper zone are used as sources of indirect heat exchange fluid to reboil the prefractionation zone and heat the feed to the isostripper zone.

In accordance with another embodiment of the invention, the overhead from the prefractionation zone comprising propane and lighter materials is condensed and contacted with relatively pure HF to remove organic fluoride prior to being subjected to fractionation at higher pressure for recovery of propane, and relatively pure HF is used as at least a part of the source of HF for contacting condensate to defluorinate, or to remove organic fluorides from same.

The process of this invention can be employed to alkylate an isoparaffin with different olefins or to separately alkylate an isoparaffin with one olefin or a mixture of olefins.

The preferred olefins in the process are propylene and butenes, but any $C_3$ to $C_7$ olefins can be used. Isobutane is preferred as the isoparaffin, but $C_5$ to $C_8$ isoparaffins can also be used, depending on the alkylate desired. The alkylation temperature can range from about 40° F. to about 200° F.; however, when alkylating isobutane with a butene or mixture of butenes using a hydrogen fluoride catalyst, a reaction temperature in the approximate range of 60° F. to 90° F. is now preferred; and when alkylating isobutane with propylene using an HF catalyst, a temperature in the approximate range of 100° F. to 125° F. is now preferred.

The alkylation pressure is at least sufficient to maintain the reactants and products in the liquid phase in the alkylation reactors and settler.

The mole ratio of isoparaffin to olefin is generally maintained in the range of 6:1 to 30:1, preferably about 10:1. The volume ratio of acid to hydrocarbon feed, particularly when using hydrofluoric acid, is maintained at about 0.5:1 to 6:1, preferably about 4:1.

The instant invention is primarily directed to an improved fractionation system following an alkylation process in which energy is used efficiently and effectively thereby reducing energy costs through the use of a combination of fractionation zones operated at different pressures and utilizing the heat of vaporization of HF-free isoparaffin vapors as well as alkylate product as sources of heat for indirect heat exchange for other units in the fractionation system. The isoparaffin vapor as well as the alkylate product and bottoms from the depropanizing zone are used in a number of indirect heat exchanges. The importance and desirability of this invention increase as the cost of energy increases and the need for conservation of energy continues.

A better understanding of the invention will be obtained by reference to the accompanying drawing which shows an arrangement of an apparatus representing a preferred embodiment of the invention.

Referring now to the drawing, olefin feed (1) and feed isobutane (2) are charged to an HF alkylation plant (3) along with subsequently recovered recycle isobutane (4) to effect alkylation of isobutane with olefins, e.g., propylene and butylenes.

The HF alkylation hydrocarbon effluent comprising alkylate, isoparaffin, propane, and lighter materials including HF from HF alkylation plant (3) is passed without pumping via (6) and indirect heater (16) to the low pressure prefractionator (5). A portion of the isobutane vapor (15) removed from prefractionator (5) at a locus below the feed (6) is used to preheat indirectly feed (6) and to effect cooling of the vapor isobutane which is further cooled and condensed and passed to accumulator (17) which is on level control actuating rate of flow of feed isobutane (2) to alkylation (3). The liquid from (17) is passed via (7) and, in minor part, to reflux HF rerun (not shown) and, in major part, as a portion of the isobutane recycled via (4).

Prefractionation zone (5) is operated at a lower pressure than the separation zone from which the hydrocarbon phase is separated and passed as feed to zone (5). Prefractionation zone (5) is operated under conditions of temperature and pressure sufficient to take overhead propane and lighter materials including HF, and as bottoms (8) an alkylate stream containing isobutane but substantially free of HF. The column is also operated such that a side vapor draw of isobutane (15) is made for heat exchange and recycle to the alkylation. Generally, prefractionation zone (5) will be operated at a pressure of about 100–150 psia, a top temperature of about 100°–140° F., and a bottoms temperature of about 140°–160° F.

The overhead (18) from prefractionator tower (5) comprising propane and lighter materials including HF and organic fluorides and some isobutane is condensed and passed to overhead accumulator (19). The liquid overhead condensate is removed from accumulator (19) via (20) and is admixed with high pressure liquid HF (21); and the mass is pumped via (22) to defluorinator (23). In defluorinator (23), organic fluorides contained in liquid (20) are removed from the hydrocarbon into the liquid HF. The upper phase liquid hydrocarbon (24) in part (25) refluxes tower (5) and, in part, is feed (9) for the high pressure depropanizer column (26). The HF phase liquid from defluorinator (23) is passed (not shown), without pumping, via (27) to the alkylation zone (3). Feed (9) comprising defluorinated condensate containing propane and some isobutane and HF is indirectly heated with depropanizer tower (26) bottoms (10) in exchanger (28) prior to tower (26), bottoms (10) being further cooled and recycled to alkylation (1) via (4). A portion of bottoms (10) is heated to vaporize same (not shown) and used to strip the HF rerun (not shown). Also, a portion of bottoms (10) is used as pump flush fluid via (29) for pumps (A) and (B). Overhead from depropanizer (26) is passed via (30) along with overhead (31), from HF stripper (38), to condenser (32) and to accumulator (33). Separated HF is passed via (21) as contacting HF for condensate stream (20). Hydrocarbon phase (35) from accumulator (33) in part refluxes (36) depropanizer tower (26), and the yield portion is passed via (11) as feed to HF stripper (38).

Depropanizing fractionation zone (26) is operated at a pressure somewhat higher than prefractionation zone (5) under conditions such that propane and HF are taken overhead and residual isobutane with any other heavier materials as bottoms. In general, depropanizing zone (26) is operated at a pressure in the range of 200–300 psia, a top temperature of about 140°–180° F., and a bottom temperature of about 180°–220° F.

HF stripping zone (38) is operated under conditions of temperature and pressure such that substantially all of the HF remaining in the condensate fed to the stripping zone is removed overhead and substantially HF-free propane as bottoms. The HF stripper overhead is combined with overhead from the depropanizer, cooled, and the condensate passed to an accumulator wherein the HF is removed from a lower portion thereof as relatively pure HF. The hydrocarbon phase containing some HF is removed from the accumulator and passed as feed to the HF stripper.

Bottoms liquid from HF stripper (38) is cooled and removed at (12) and passed to HF removal, e.g., a solid KOH treater, to yield LPG propane liquid [the amount of (12) equals that propane charged to and produced in HF alkylation zone (3)]. A portion of the propane yield (12) is used via (39) as pump flush at pump (C).

A lower side-draw (40) from prefractionator (5) indirectly is heated in heat exchanger (42) by hot isobutane vapor (13) removed overhead from high pressure isostripper (50), described below. This heated stream (40) is returned to prefractionator tower (5) via (41) as part of the heat supplied to a lower portion of prefractionator tower (5). The bottoms (isobutane, normal butane, and alkylate) yield (8) removed from tower (5) is pumped (to increase pressure thereon), is preheated indirectly in exchanger (51) by the bottoms alkylate yield (14) from isostripper tower (50) and is passed as feed to isostripper tower (50). The alkylate yield (14), removed as bottoms from tower (50), after indirectly preheating the tower (50) feed (8) is also used to indirectly reboil tower (5) at (43) located in a lower portion of tower (5). Trim steam heating (44) is also used to reboil tower (5). Isostripper tower (50) is reboiled by fired reboiler (52). Isobutane (13), after passing through exchanger (44), also preheats stream (8) in exchanger (45), and is further cooled and condensed and recycled to alkylation plant (3) via conduit (4).

Isostripper (50) is operated at a pressure substantially higher than prefractionation zone (5) and under conditions such that substantially only isoparaffin, e.g., isobutane, is taken overhead and the alkylate substantially free of other materials as bottoms. In general, isostripper zone (50) is operated at a pressure of about 200–300 psia, a top temperature of about 200°–220° F., and a bottoms temperature of about 400°–450° F.

Prefractionator (5) is operated at relatively low pressure so that the tower can be reboiled by the isobutane-rich overhead vapor (13) from isostripper (50) which is operated at relatively high pressure [such high pressure being effected by inexpensive pumping of liquid feed (8) from the low pressure of tower (5) to the high pressure of tower (50)].

This operation, as above described, using low pressure prefractionation (5) and high pressure isostripping (50), saves about 30 percent of normal heat requirements in the HF alkylation plant.

| Typical Operating Conditions and Flows (Calculated) | |
|---|---|
| (A) Operating Conditions: | |
| HF Alkylation (3): | |
| Pressure, psia | 150 |
| Temperature, °F. | 90 |

-continued

| Typical Operating Conditions and Flows (Calculated) | |
|---|---|
| (A) Operating Conditions: | |
| Total IC$_4$/Olefin Mole Ratio | 20:1 |
| HF/Total Hydrocarbon Vol. Ratio | 4:1 |
| Prefractionator (5): | |
| Pressure, psia | 120 |
| Temperature, °F.: | |
| Top | 120 |
| Bottom | 150 |
| Accumulator (19): | |
| Pressure, psia | 110 |
| Temperature, °F. | 100 |
| Accumulator (17): | |
| Pressure, psia | 110 |
| Temperature, °F. | 125 |
| Defluorinator (23): | |
| Pressure, psia | 245 |
| Temperature, °F. | 100 |
| Depropanizer (26): | |
| Pressure, psia | 255 |
| Temperature, °F.: | |
| Top | 160 |
| Bottom | 200 |
| HF Stripper (38): | |
| Pressure, psia | 300 |
| Temperature, °F.: | |
| Top | 129 |
| Bottom | 139 |
| Accumulator (33): | |
| Pressure, psia | 245 |
| Temperature, °F. | 100 |
| Isostripper (50): | |
| Pressure, psia | 245 |
| Temperature, °F.: | |
| Top | 207 |
| Bottom | 416 |

| | (B) Flow Rates, Barrels/Day | | | | | | | | | | | | | |
|---|---|---|---|---|---|---|---|---|---|---|---|---|---|---|
| | | | | | Stream | | | | | | | | | |
| Composition | (1) | (2) | Total (1&2) | (4) | Total (1,2,&4) | (6) | (7) | (8) | (9) | (10) | (11) | (12) | (13) | (14) |
| HF | — | — | — | 5 | 5 | 730 | 5 | — | 122 | — | 4 | — | 40 | — |
| Propane | 244 | 107 | 351 | 1,190 | 1,541 | 1,562 | 1,002 | 39 | 521 | 156 | 684 | 351 | 62,849 | 26 |
| Isobutane | 1,466 | 5,080 | 6,546 | 107,335 | 113,881 | 106,677 | 30,579 | 62,875 | 13,223 | 13,217 | 9 | 5 | — | — |
| Butylenes | 5,617 | — | 5,617 | — | 5,617 | — | — | — | — | — | — | — | — | — |
| Normal Butane | 358 | 160 | 518 | 3,791 | 4,309 | 4,338 | 959 | 2,986 | 393 | 393 | — | — | 2,468 | 518 |
| Isopentane Plus | — | — | — | 1,400 | 1,400 | 11,518 | 208 | 11,285 | 25 | 25 | — | — | 1,170 | 10,115 |
| Totals | 7,685 | 5,347 | 13,032 | 113,721 | 126,753 | 124,825 | 32,753 | 77,185 | 14,284 | 13,791 | 697 | 356 | 66,527 | 10,659 |

Note:
The above figures do not, in all cases, include pump flushes and HF rerun reflux and stripping fluid quantities.

By operating the prefractionator (5) at this relatively low pressure, substantially all of the HF in feed (6) is removed overhead at (18), and therefore, the HF-free bottoms (8) can be passed (pumped) to isostripper (50) operated at high pressure and high temperature. Because stream (8) is free of HF, tower (50) can be so operated with no HF corrosion problems. The high pressure, high temperature operation of tower (50) produces high temperature vapor (13) and high temperature liquid (14) which can now be used as indirect heat exchange fluids, especially for reboiling the low pressure prefractionator (5), as illustrated in the figure, wherein considerable isobutane is removed from feed (6).

The process of the invention can save about thirty percent of utilities (heat) costs or requirements while operating at the conventional, relatively high, isobutane-to-olefin mol ratio of 12 to 1 in the alkylation plant (3). At the same heat requirements now conventionally used in HF alkylation, the present invention can operate at an extremely high isobutane-to-olefin ratio of about 20 to 1, and thereby produce even higher octane alkylate using the conventional heat requirements.

It is pointed out that the liquid hydrocarbon (6) from alkylation plant (3) must be heated to vaporize the isobutane from the alkylate product. This thusly produced vaporized isobutane must be condensed and cooled before this isobutane can be recycled (4) to alkylation plant (3). The major heat supplied to this separation is from the fired reboiler (52) on the isostripper tower (50). Since prefractionator (5) is operated at relatively low pressure, even at a pressure lower than HF alkylation plant (3), a great quantity of isobutane is removed from the alkylate in this tower (5), and substantially all of the HF is removed from the bottoms yield (8) in this tower (5). Since bottoms (8) is depleted of a substantial quantity of isobutane and is free of HF, bottoms (8) can be charged to this high pressure, high temperature isostripper tower (50) with now no HF corrosion problems, and because less feed (8) is charged to high pressure tower (50), and since tower (50) can be now operated at high pressure, isostripper tower (50) can be considerably smaller than the conventionally employed isostripper tower.

I claim:

1. A process for the separation of the hydrocarbon liquid phase recovered from the effluent of an HF alkylation in a fractionation system employing low pressures in an initial fractionation followed by high pressures in subsequent fractionations which comprises:

(a) passing said hydrocarbon liquid phase comprising alkylate, unreacted paraffin, propane, and small amounts of HF to a first fractionation zone operated at pressures in the range 100–150 psia, (b) subjecting said hydrocarbon liquid phase in said first fractionation zone to fractionation conditions sufficient to remove (1) an overhead stream comprising propane and lighter materials including trace amounts of HF and some isoparaffin, (2) a side vapor stream comprising isoparaffin, and (3) a bottoms stream substantially free of HF comprising isoparaffin and alkylate;

(c) condensing said overhead (1) and passing condensate formed to a second fractionation zone operated at a higher pressure than said pressures in said first fractionation zone under fractionation conditions sufficient to separate a second overhead stream comprising propane and a second bottoms stream comprising isoparaffin, and recycling said isoparaffin to said HF alkylation;

(d) passing said bottoms stream (3) to a third fractionation zone operated at a higher pressure than said pressures in said first fractionation zone and therein subjecting same to fractionation conditions sufficient to remove a third overhead stream comprising isoparaffin vapors and to recover a third bottoms stream comprising alkylate;

(e) passing said third overhead stream obtained in (d) in indirect heat exchange with a lower portion of said first fractionation zone and recycling said stream after said heat exchange to said alkylation; and (f) passing said third bottoms in (d) in indirect heat exchange with said bottoms stream (3) to said third fractionation zone and in indirect heat exchange with the lower portion of said first fractionation zone prior to recovery of said third bottoms in step (d) as alkylate product.

2. A process according to claim 1 further comprising the steps of:

(g) contacting said condensate from said first fractionation zone with relatively pure HF to defluorinate said condensate, phase separating said condensate into an HF phase and a hydrocarbon phase which is returned in part as reflux to said first fractionation zone and the remainder is passed as feed to said second fractionation zone in (c) and recycling HF separated from defluorinated condensate to said alkylation.

3. A process according to claim 2 wherein HF separated from defluorinated condensate and from said second fractionation zone are combined and in part used to contact said condensate to defluorinate same and the remainder is recycled to the alkylation.

4. A process according to claim 1 wherein said second fractionation is operated at a pressure in the range of about 200–300 psia, and said third fractionation zone is operated at a pressure in the range of about 200–300 psia.

5. A process according to claim 1 wherein said third overhead stream comprising isobutane vapor is used to indirectly reboil said first fractionation zone and then indirectly preheat said bottom stream (3) to said third fractionation zone;

said third bottoms comprising alkylate is used to indirectly preheat said third fractionation zone feed and then indirectly reboil said first fractionation zone;

condensate from said first fractionation overhead is contacted with relatively pure HF to remove organic fluoride;

said defluorinated condensate is passed to said second fractionation zone and the propane overhead is removed therefrom, condensed, and the condensate formed is passed to an HF stripper to remove remaining HF leaving a propane product substantially free of HF;

combining HF removed from said HF stripper with overhead from said second fractionation and recovering relatively pure HF from said condensate; and utilizing said relatively pure HF as at least a portion of the HF used to defluorinate said condensate obtained from the overhead of said first fractionation zone.

* * * * *